US005653928A

United States Patent [19]
Schnipke

[11] Patent Number: 5,653,928
[45] Date of Patent: Aug. 5, 1997

[54] METHOD FOR ASSEMBLING A SURGICAL STAPLING CARTRIDGE

[75] Inventor: Leonard H. Schnipke, Cloverdale, Ohio

[73] Assignee: Schnipke Family Partnership, Ottoville, Ohio

[21] Appl. No.: 490,767

[22] Filed: Jun. 15, 1995

[51] Int. Cl.$^6$ .................... B29C 37/02; B29C 65/00; B23Q 3/00
[52] U.S. Cl. .................... 264/138; 264/249; 29/464; 29/811.2
[58] Field of Search .................... 264/154, 155, 264/156, 158, 249, 297.8, 138; 227/107, 119, 176.1; 29/464, 811.2

[56] References Cited

U.S. PATENT DOCUMENTS 4,193,181  3/1980  Boulanger et al. .................... 264/249
5,392,509  2/1995  Cheswick .................... 29/818

*Primary Examiner*—Jan H. Silbaugh
*Assistant Examiner*—Robin S. Gray
*Attorney, Agent, or Firm*—Kremblas, Foster Millard & Pollick; Sidney W. Millard

[57] ABSTRACT

Method for assembling staple drivers in a cartridge to be used during surgery includes a fixture having tapered converging passageways to guide staple drivers into alignment with pockets in the cartridge. After the staple drivers are properly in place to be pushed into the pockets of the cartridge, a plunger with blade-shaped projections descends such that the blades project through the fixture and the passageways therein to push the drivers into the pockets. To prevent the drivers from falling out of the pockets through the entrance opening where they were inserted, a pocket locking or blocking element is applied to the cartridge after the drivers are in the pockets.

8 Claims, 6 Drawing Sheets

METHOD FOR ASSEMBLING A SURGICAL STAPLING CARTRIDGE

FIELD OF THE INVENTION

This invention relates to cartridges to be assembled with a surgical instrument to guide a blade during surgery and thereafter staple the edges of the incision together.

BACKGROUND OF THE INVENTION

In the field of microsurgery, a reusable surgical instrument is assembled in well-known conventional fashion where the cutting blade is mounted to traverse a specific pattern guided by elements of the surgical instrument. The blade and associated guide elements are mounted in somewhat remote location with respect to the hands of the surgeon. A conventional feature of the surgical instrument is a staple cartridge which is used only once.

The cartridge is a generally elongated rectangular plastic body which includes a channel formed longitudinally in the elongated body. The channel is a guide for the surgical blade which is secured on the surgical instrument. The structure of the instrument and cartridge which are well-known in the industry include a plurality of small staples aligned in the cartridge parallel with the guide channel. After the blade makes its cut and other necessary surgical operations are performed, a remote actuator causes each side of the incision to be stapled together for obvious reasons.

The particular structure for manipulating the blade and actuating the staple operation is not a part of this invention. It is well-known in the industry and there is no need to describe the same.

Due to the minute structure involved in the surgery for which this invention is made, there may be as many as fifty or more staples on each side of a two inch incision which are actuated simultaneously to close the wound. The staples are pushed by drivers through the tissues around the wound and against an anvil on the surgical instrument. The anvil deflects the points of the staples into clasping position. Assembling of the drivers into the cartridge and maintaining them in place to drive the staples into the tissues is a labor intensive chore.

The present system for mounting the staple drivers in pockets in the cartridge is to form a plastic tree having aligned branches with staple drivers integrally formed on one end of each of the aligned branches. The already-formed conventional cartridge is placed in a fixture and the tree bearing the staple drivers is hand manipulated to place the drivers adjacent the entrance to pockets in the cartridge. Each driver is pressed into the pocket in the cartridge by the fingers of the assembler. Separation of the individual drivers from the branch of the tree on which it is mounted is accomplished by a flexing of the branches of the tree manually to break off the staple drivers. Then, a hand-manipulated blade or prong is used to press each staple driver down into the cassette to near the pocket opening on the opposite side of the cassette.

Unfortunately, the finger operation of pressing each driver into a pocket, the flexing of the branches which also tilts the drivers and the subsequent pressing from the hand operated prongs can misalign some of the drivers within the pockets.

The size of the pockets and the periphery of the drivers may have a slight variation due to the minute structure involved and the fact that both the cartridge and the staple drivers are formed of thermoplastic resin, could cause some play in the assembly and that can cause an alignment problem. Particularly, an inversion of the cartridge could result in some drivers being displaced from their pockets due to gravity and/or impacts during assembly and packaging, and even during the mounting of the replacement cartridge with the surgical instrument. Obviously, if the staple driver is not in place, there will be no staple at that point in the incision.

This invention solves the problem of assuring driver alignment in the pockets, accelerates the assembling operation and provides a block or lock mechanism to prevent the unintentional displacement of staple drivers from pockets in the cartridge after initial assembly.

SUMMARY OF THE INVENTION

A mechanical assembling apparatus which is manually manipulated to a certain extent is employed in the procedure for placing staple drivers in the pockets of conventional staple holding cartridges. Several pieces of assembling apparatus are mounted on a frame and one piece includes a pattern to facilitate the insertion of the empty cartridge into a trough which is configured to prevent improper insertion.

Immediately above the trough is a fixture having a plurality of downwardly converging passageways structured to receive small plastic staple drivers. A plurality of the staple drivers are hand manipulated into position in the passages of the fixture by the conventional tree and branch combination. The converging passageways allow the staple drivers to descend partially into the entrance to the pockets of the cartridge while part of each staple driver remains in the narrowest part of the converging passages. With this confining mechanism, separation of the staple drivers from the branches of the tree are accomplished by a vertical pivoting of the tree trunk which ultimately breaks the staple drivers from the ends of the branches. The narrow exit from each passage combines with the pocket entrance to hold each driver in alignment with its pocket.

This driver separation is followed by a manual actuation of a piston and cylinder combination which drives a plate downwardly from above the fixture. A plurality of plungers in the form of thin blades project below the descending plate and each blade penetrates a passageway in the fixture to engage the exposed rear end of each staple driver to urge it into its proper pocket while the converging passageways of the fixture guide the staple drivers into proper alignment within each pocket. Each driver has a geometric shape and size generally conforming to the shape and size of the pocket into which it is inserted. Misalignment results in the improper sliding movement of the driver in the pocket.

After the plungers retract, the cartridge bearing the assembled staple drivers is removed to another work station where it is inserted longitudinally into a bracket; the bracket is configured to receive the cartridge only in proper orientation and to a proper depth in the bracket such that it is immediately below a reciprocable plate bearing chisel points in alignment with each other and offset to one side of the entrance openings of the pockets in the cartridge. Manual actuation of a plate supporting the chisel points causes the chisels to be heated and descend into engagement with the surface of the cartridge adjacent the entrance to the pockets and, by virtue of the heat, causes plastic deformation of the geometric configuration of the entrance opening to the pockets and thereby prevents accidental displacement of the drivers from the pockets by gravity or impacts.

It should be clear that other ways for blocking the entrance to pockets could serve the same purpose without departing from the spirit of the invention. For example, a hot melt could be ejected along the edge, a wire could be strung longitudinally to cover the entrances to the pockets with each end of the wire attached to an end of the cartridge, or some snap structure could allow a thin plate to be snapped to the cartridge to cover the pocket entrances. All such alternatives are within the inventive concept.

After the pocket entrances are suitably blocked, the cartridge is removed to another location where a staple is placed in each pocket through a pocket opening on the opposite side of the rectangular shaped cartridge from the entrance openings. This procedure is not illustrated in any detail in this application because it is a conventional procedure having no novel features under this invention.

Objects of the invention not understood from the above, will be fully appreciated upon a review of the drawings and the description of the preferred embodiments which follow.

DETAILED DESCRIPTION OF THE PREFERRED EMBODIMENTS

Figure 1:
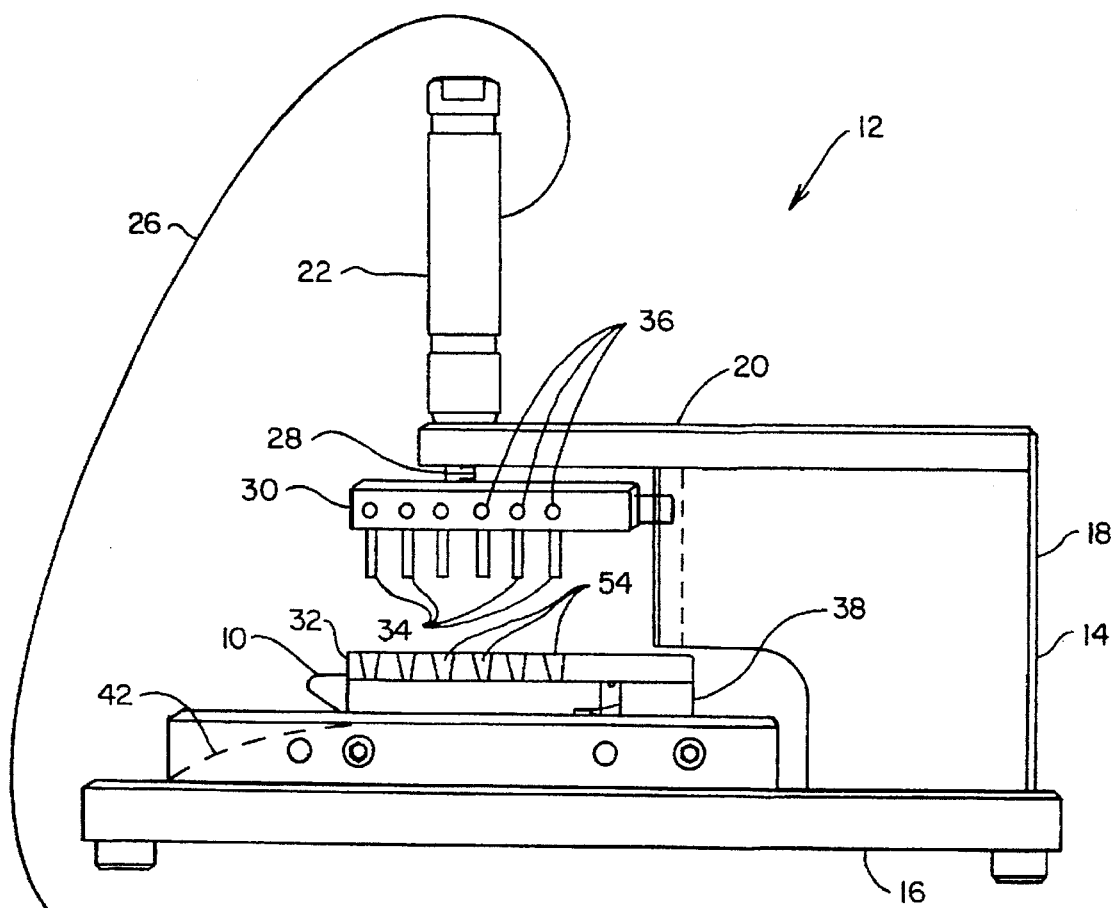
FIG. 1 is a side elevational view of assembly apparatus for mounting staple drivers in a cartridge.

FIG. 1 illustrates apparatus for inserting staple drivers into pockets of a cartridge 10. The shape of the cartridge is conventional structure and is molded or formed of a thermoplastic resin. The preferred resin is phenylene oxide sold under the General Electric trade name NORYL SPN 420. Phenylene oxide has a melting point above about 375° F.

Figure 2:
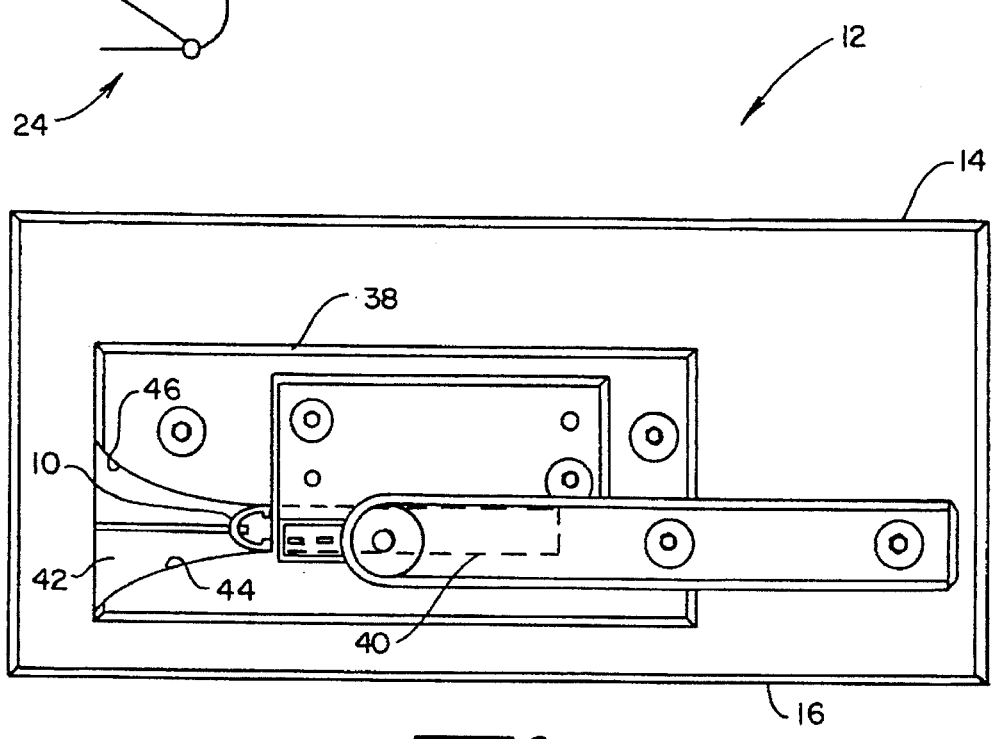
FIG. 2 is a top plan view of the apparatus of FIG. 1.

The apparatus of FIGS. 1 and 2, shown generally at 12 includes a framework 14 supported on a base 6 and having an upwardly projecting standard 18 with a forwardly projecting support arm 20. A piston and cylinder combination 22 is mounted above support arm 20 at the forward end thereof. The piston and cylinder combination is illustrated schematically as being actuated by a foot pedal 24 connected to piston and cylinder combination 22 by line 26. Foot pedal 24 is in fact merely a switch which may be suitably connected to electric, pneumatic, or hydraulic systems to cause piston and cylinder combination 22 to reciprocate vertically.

A piston rod 28 projects from piston and cylinder combination 22 and is connected to a plate 30 by threads which may be used to adjust the spacing and length of the reciprocation stroke of the plate 30 with respect to a fixture 32 mounted below plate 30. A plurality of blade shaped plungers 34 are secured in holes (not illustrated) in the bottom of plate 30 and secured in place by set screws 36.

Figure 4:
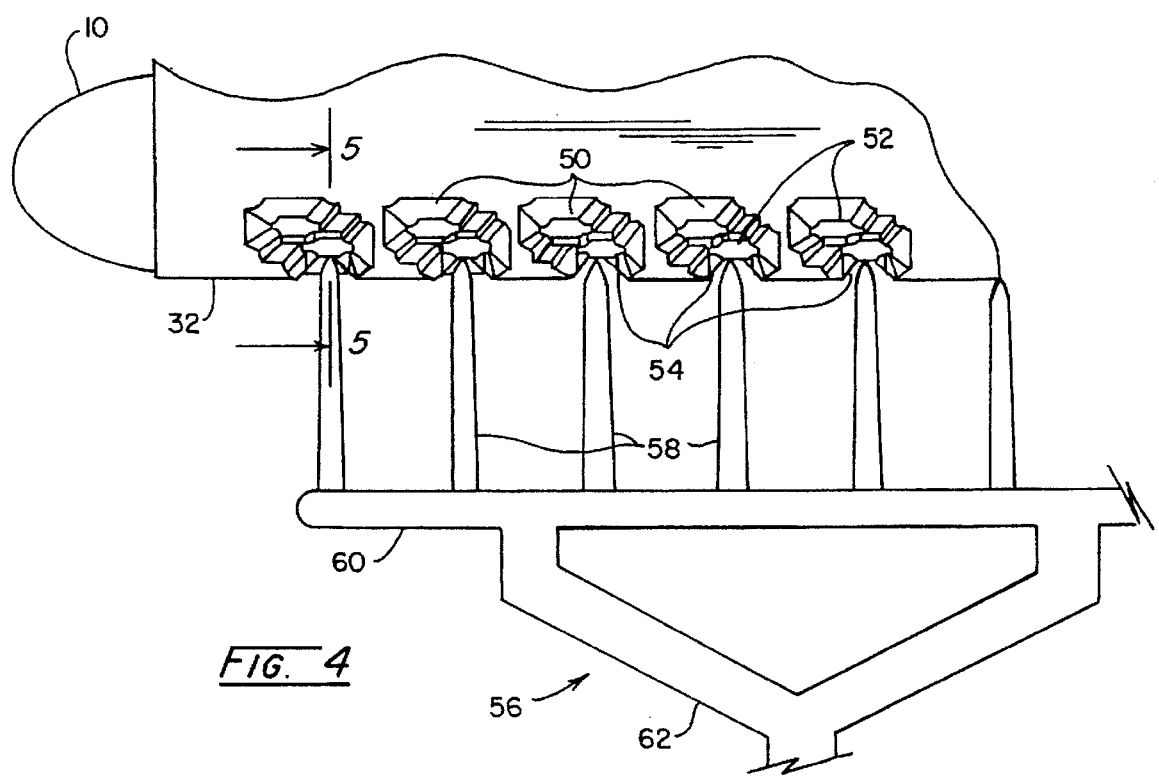
FIG. 4 is a fragmentary sectional view taken along line 4—4 of FIG. 3.
Figure 5:
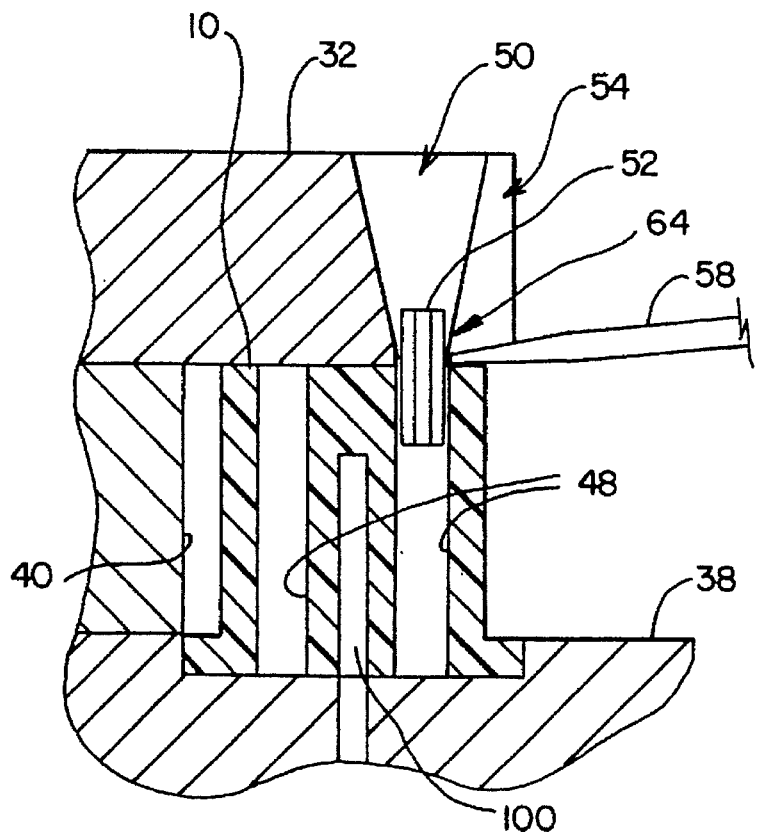
FIG. 5 is a fragmentary sectional view taken along line 5—5 of FIG. 4.

A support block 38 is secured on base 16 to provide a trough 40 which is configured to receive cartridge 10 between sloping converging walls 42, 44, 46, such that cartridge 10 cannot be inserted incorrectly and also such that pockets 48 in one side of cartridge 10 are vertically aligned with passages 50 formed in fixture 32. Note that each passage 50 extends vertically from the top of fixture 32 toward the bottom which is juxtaposed to cartridge 10 and as best seen in FIGS. 4 and 5, passages 50 are of a specific geometric shape to accommodate the shape of a double staple driver 52 as will be explained in more detail subsequently. Slots 54 extend through one side of fixture 32 for reasons which will also be explained subsequently.

Looking to FIGS. 3, 4, 5 and 6, a tree 56 formed of thermoplastic resin includes a plurality of branches 58 which are horizontally aligned with each other and project from a straight bar 60 connected to a trunk 62. The tree illustrated in FIG. 6 includes only a single molded double staple driver 52 for convenience. In normal practice, a double staple driver is integrally formed at one end of each branch 58 and connected thereto by a very narrow plastic connection which allows breakage and separation of each driver 52 upon vertical bending of branches 58 with respect to drivers 52 when the drivers 52 are trapped in the exit or narrowest part 64 of converging passages 50 and the entrance opening to pockets 48, as best illustrated in FIG. 5.

Looking now to FIGS. 7 through 11, after the apparatus 12 is used appropriately to place staple drivers 52 within pockets 48 of cartridge 10, the cartridge is removed and delivered to a staking apparatus 66. Staking apparatus 66 includes a bracket 68 formed of a pair of blocks 70,72. A substrate 74 supports blocks 70,72 which are suitably configured to control the insertion in straight line horizontal fashion of cartridge 10 such that the cartridge cannot accidentally be inserted in the wrong way and insuring that after proper insertion, cartridge 10 will be properly aligned with a support plate 76. Support plate 76 includes a plurality of downwardly projecting chisel blades 78 each having a sharp edge 80 which is formed by two converging surfaces 82,84. Surface 82 is a generally flat vertical surface while surface 84 is concave, diverging outwardly.

In practice, blocks 70,72 are actuated to move into proper position by automatic mechanical means. Staking apparatus 66 is enclosed in a transparent box as a safety feature. This box minimizes injury of the machine operator due to heat and improper placing of hands under the plate 76.

A second piston and cylinder combination 86 includes a piston rod 88 to move support structure 90 up and down vertically such that chisel edges 80 engage the upper surface of cartridge 10 to deform the thermoplastic resin forming the cartridge. The resulting plastic deformation blocks or locks the entrance 92 of pockets 48 to thereby prevent staple drivers 52 from being accidentally dislodged or displaced from the cartridge by gravity or impacts during packaging.

Figure 7:
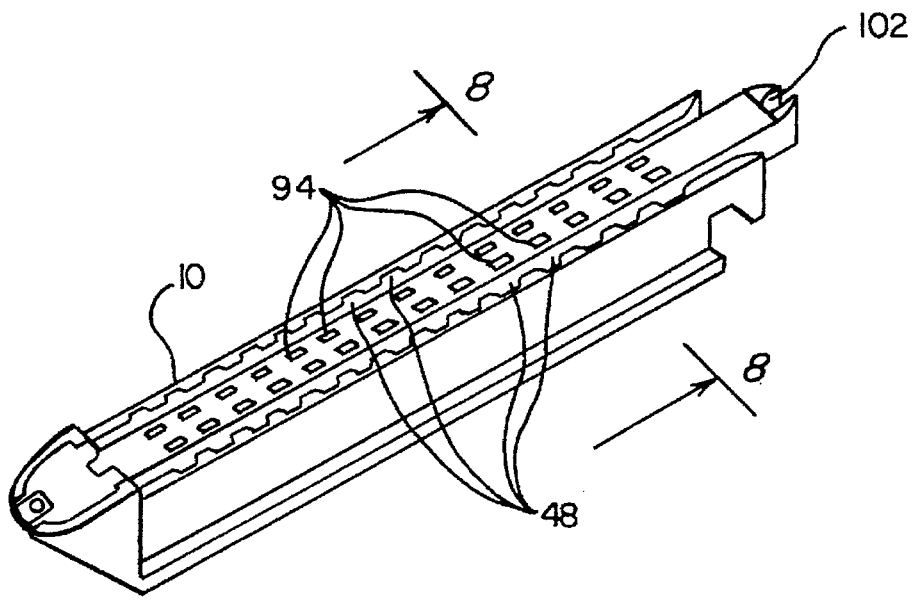
FIG. 7 is a perspective view of one side of the cartridge with the entrance opening to the pockets facing upward and showing deformed areas at each pocket.
Figure 8:
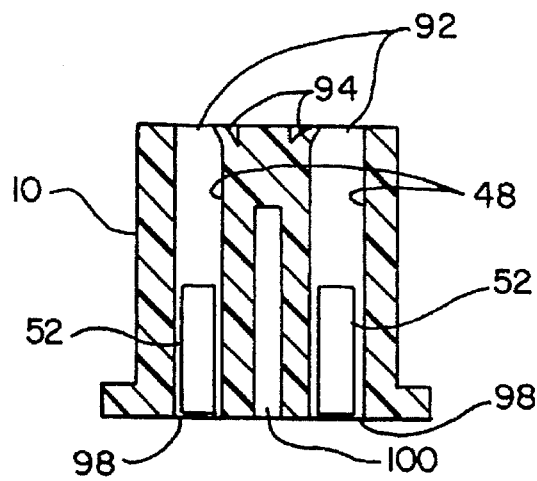
FIG. 8 is a sectional view taken along line 8—8 of FIG. 7.
Figure 9:
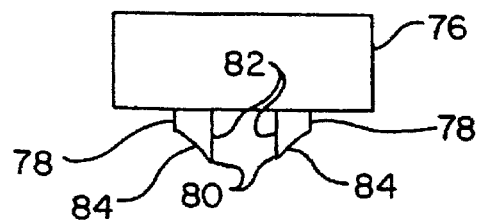
FIG. 9 is an enlarged end view of protruding chisels on the bottom of a plate.

Note the cuts 94 in the upper surface of cartridge 10 illustrated best in FIGS. 7 and 8. To facilitate the deformation of the plastic of cartridge 10, a heater (not shown) is provided to heat the chisels 78 to a temperature in the range 325° to 375° F. and preferably about 350° F. The preferred resin of cartridge 10 has a melting point above about 375° F. and a temperature above that tends to make the plastic sticky and over a period of time, the plastic tends to coat the chisel surfaces 84. Similarly, it has been discovered that heating to a temperature below about 325° F. is inadequate to cause plastic flow conveniently and occasionally, a crack or fracture occurs because of the relatively small structures involved. It will be noted that the location of the cuts 94 in the surface of cartridge 10 is on an inside surface such that the plastic is deformed in an outward direction over pocket openings 92 and the curvature of surfaces 84 tends to cause the plastic to flow in that direction.

Figure 10:
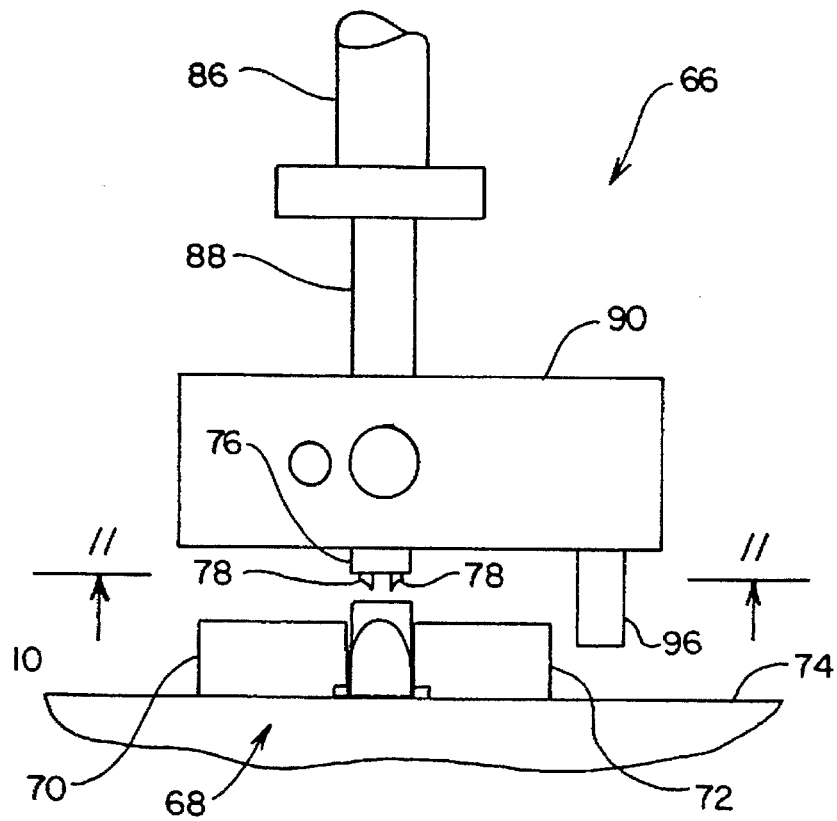
FIG. 10 is a fragmentary end elevational view of the staking apparatus of this invention showing the plate and chisels of FIG. 9 in operative position.
Figure 11:
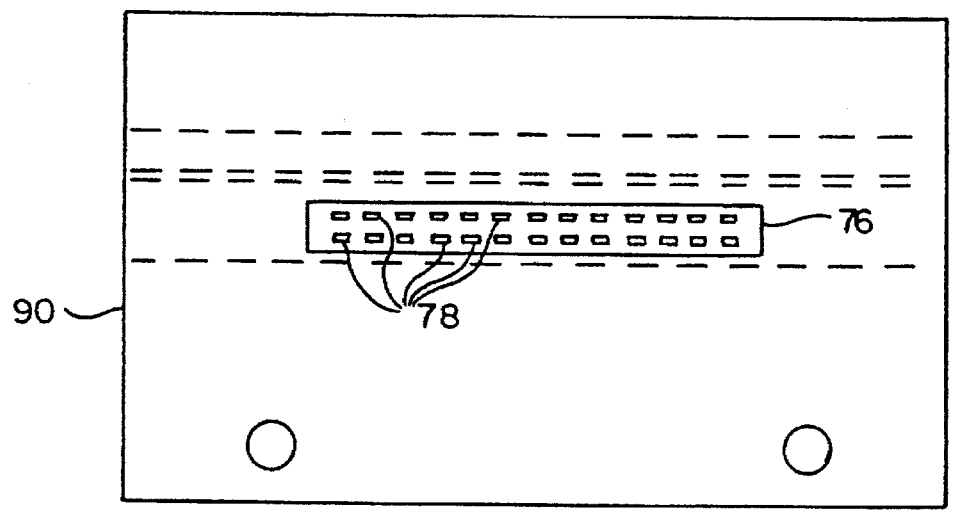
FIG. 11 is a sectional view taken along line 11—11 of FIG. 10.

It will be observed in FIG. 10 that a stop peg 96 extends from support 90 such that it will engage substrate 74 to limit the downward movement of support plate 76 and chisels 78 to thereby control the degree of plastic deformation.

An observation of FIGS. 5 and 8 shows the staple drivers loosely mounted in the pockets 48 of the generally rectangularly shaped elongated cartridge That is not really an accurate reflection of how they really work. There is very little play between the side walls of the pockets 48 and the periphery of the drivers 52 and they are configured in the preferred embodiment as a six-sided geometric configuration. Specifically, the six-sided element for driver 52 is depressed into the bottom part of pocket 48 near the generally six-sided pocket opening 98 by the plungers 34 when the piston and cylinder combination 22 is actuated manually by a foot, thigh or hand engaging the switch 24. The close tolerances between the lower or narrowest part 64 of passage 50 in fixture 32 and the close tolerance between the periphery of driver 52 and pocket opening 98 combine to keep and guide the driver into proper alignment upon its actuation at a later time when the cartridge is placed in operation as a replacement part in a surgical tool. The term "driver" is used interchangeably with the term "double driver" and the equivalent double driver has twelve sides fitting into two adjoining pockets. The concept remains the same.

Figure 12:
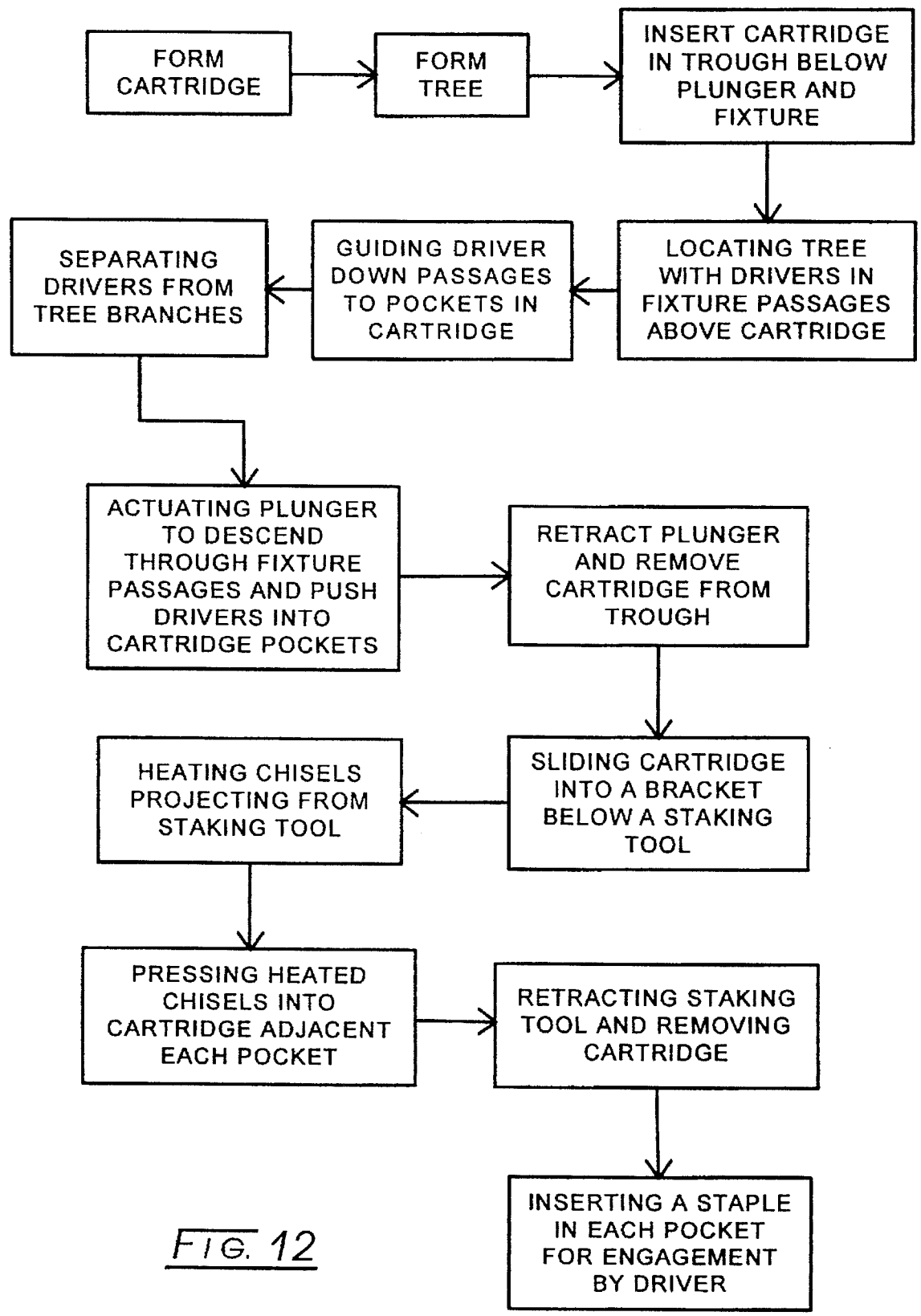
FIG. 12 is a block diagram of the procedural sequence of this invention.

Looking to FIG. 12, in operation, the cartridge 10 is ordinarily formed by injection molding using phenylene oxide of a specific color. Blue, red and other colors have specific meanings in the surgical field. The formation of the cartridge of elongated generally rectangular shape is conventional. It includes a guide channel 100 in one face to accommodate and guide a cutting blade which is actuated by other elements of the surgical instrument which is not relevant to this particular invention.

The incision made by the blade passing through guide channel 100 will later have its side edges stapled together by a plurality of staples (not illustrated) which are inserted into the cartridge through pocket openings 98. Each staple fits in a pocket 48 to be expelled by a driver 52 at a suitable time to be decided by a surgeon.

Figure 6:
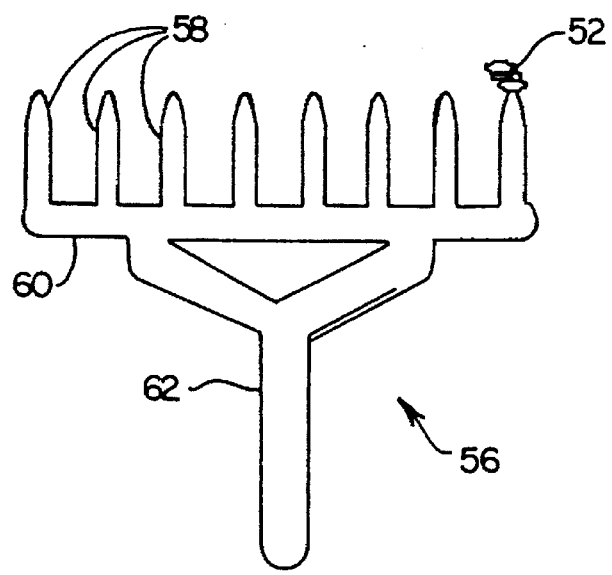
FIG. 6 is a top plan view of a tree with a plurality of branches and with a pair of staple drivers mounted on one end of one of the branches.

A tree 56 illustrated in FIG. 6 is formed in conventional fashion with one or a double set of staple drivers 52 formed integrally with one end of each branch 58 of the tree.

The formed cartridge is inserted into a trough 40 (see FIGS. 3 and 5) below a plate 30. A fixture 32 is located intermediate the plate 30 and the cartridge 10.

Figure 3:
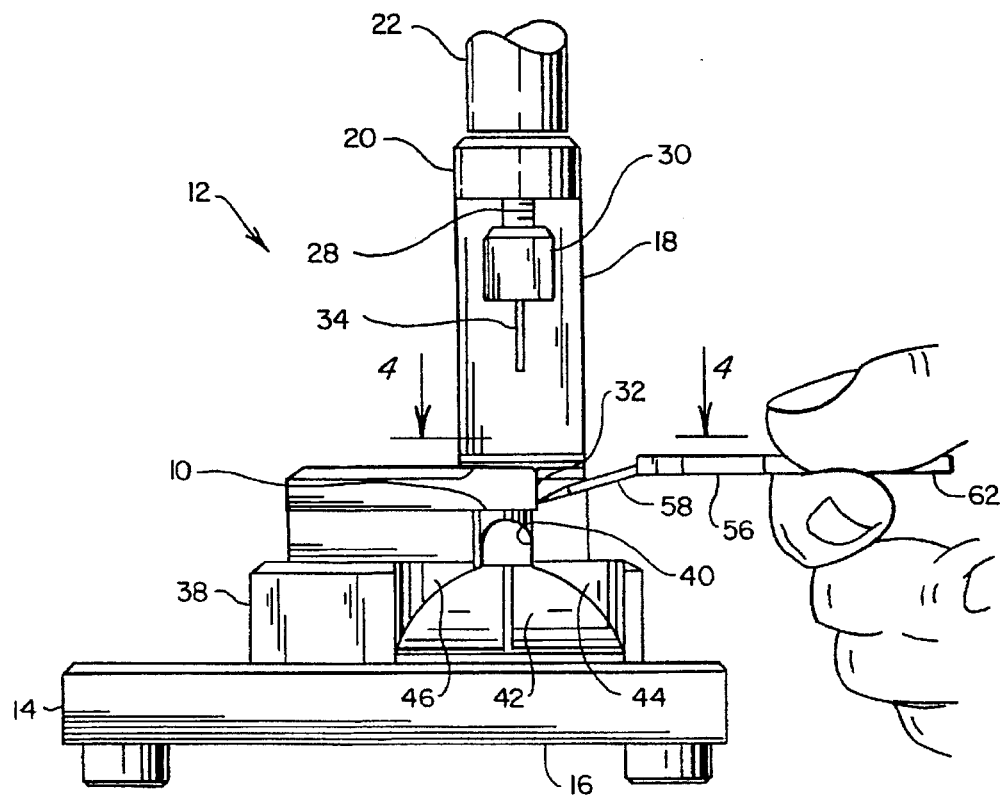
FIG. 3 is a left hand side elevational view of the apparatus of FIG. 1.

The tree 56 bearing the staple drivers 52 is hand manipulated such that the drivers slide into tapering passages 50 as illustrated in FIGS. 3, 4 and 5. It will be noted in FIG. 4 that the tapering converging passages 50 are of the same general geometric shape as the drivers mounted on the ends of branches 58. In the illustrated embodiment, a double set of drivers is mounted on each branch with the drivers being transversely offset with respect to each other and transversely of channel 100. In this instance, the double driver will drive two staples in tandem because the drivers are structured to move in tandem. It is clear that a single driver could be mounted in each pocket without any connection to any other driver. However, the drivers used in conventional apparatus are double drivers as illustrated.

Note that the narrow supporting portion of the branches 58 connected to the drivers slides downwardly in slots 54 until the branch 58 engages the upper surface of cartridge 10 (FIG. 5) with the driver 52 partially within the cartridge 10 and partially within the fixture 32. The narrow exit portion 64 of the fixture 32 closely surrounds the driver 52 such that it remains properly aligned in its geometric shape with the corresponding geometric shape of the pocket 48. Separation of the branches 58 from the drivers 52 is accomplished by raising and lowering the trunk 62 of the tree and wiggling it in a vertical plane to break the drivers from the branches while the throats 64 of the passages 50 and the pocket surfaces hold the driver in stationary position. A couple of bends accomplishes the desired separation.

After separation from branches 58, drivers 52 are pushed to near the bottom of pockets 48 by actuation of switch 24 which urges plunger plate 30 downward and the plungers 34 engage the trailing surfaces of drivers 52 to push them downward. The length of the plungers 34 and the thickness of the fixture 32 combine to serve as a stop in the downward passage of plungers 34 according to the desired result and this is accomplished by the threaded connection between plate 30 and piston rod 28.

After plungers 34 are retracted, cartridge 10 is extracted from trough 40 and taken to another piece of apparatus 66 as illustrated in FIG. 10. The properly aligned and oriented cassette cartridge 10 is inserted longitudinally into bracket 68 formed by blocks 70,72 below staking tool 66.

A heater is actuated to heat chisels 78 to a temperature in the range of 325° to 375° F. which is followed by actuation of piston and cylinder combination 86 to drive chisel plate 76 and chisels 78 downward into the upper surface of cartridge 10 to effect a blocking or sealing of the pocket entrances 92. Note in FIGS. 7 and 8 that one chisel 78 is oriented to deform the plastic surface of the cartridge adjacent each pocket 48.

After the staking tool is retracted and the cartridge removed, it is taken to another work station where a staple is inserted into each pocket in engagement with a driver for use in a surgical operation.

A component of the cartridge includes an element 102 which prevents more than one use of the cartridge in each surgical operation. Accordingly, the cartridge with the incorporated drivers and staples is a replacement part for a surgical instrument which involves a cutting blade. The remainder of the surgical instrument may be reused a plurality of times with replacement cartridges and perhaps with replacement cutting blades, but that does not relate to this particular inventive concept. The cartridge of this invention is a replaceable, one-time component which is replaced with each surgical procedure.

Having described the invention in its preferred embodiments, it will be clear that modifications may be made to the structure and the procedural steps as disclosed without departing from the spirit of the invention. It is not intended that the words used to describe the invention nor the drawings used to illustrate the same, be limiting on the invention. Rather it is intended that the invention be limited only by the scope of the appended claims.

I claim:

1. A process for assembling a surgical stapling cartridge comprising:

providing an elongated cartridge of generally rectangular cross-section and having a channel formed in one side of said rectangular cross-section, said channel serving to accommodate and guide movement of a cutting blade, said cartridge including a plurality of pockets extending through said cartridge with pocket entrance openings and pocket exit openings formed in said one side, said pocket exit openings being aligned parallel with said channel in said one side, said pocket exit openings and said pocket entrance openings being of a geometric shape and size, providing a trough configured to receive said cartridge such that some of said plurality of pockets are aligned with a plurality of overlying plungers, inserting said cartridge into said trough with said pocket exit openings facing away from said overlying plungers, providing a guide fixture intermediate said cartridge and said plungers, said fixture including a plurality of tapered guide passages, each of said plurality of tapered guide passages being aligned with one of said pocket entrance openings, each of said plurality of tapered guide passages converging toward one of said pocket entrance openings, each of said plurality of tapered guide passages converging to guide passage exit openings generally corresponding in size and shape to one of said pocket entrance openings and said pocket exit openings, providing a tree including a plurality of branches, a staple driver connected to one end of each of a corresponding one of said plurality of branches, each said staple driver being linearly aligned on said corresponding one of said plurality of branches, providing said plurality of staple drivers with a geometric shape and size corresponding generally to said geometric shape and size of said pocket entrance openings and said pocket exit openings and said guide passage exit openings, simultaneously sliding each said staple driver into a corresponding one of said plurality of tapered guide passages and toward a corresponding one of said plurality of pockets by manipulating said tree until each said staple driver is partially within said corresponding one of said plurality of tapered guide passages and in alignment with said corresponding one of said plurality of pockets in said cartridge, simultaneously separating each said staple driver from each said corresponding one of said plurality of branches and maintaining each said staple driver partially within a corresponding one of said plurality of tapered guide passages, and simultaneously pushing each one of said plurality of overlying plungers into a separate one of said plurality of tapered guide passages to thereby engage and push a corresponding staple driver from said corresponding one of said plurality of tapered guide passages through a corresponding one of said pocket entrance openings and into said corresponding one of said plurality of pockets.

2. The process of claim 1 including removing said cartridge from said trough with each said staple driver within a corresponding one of said plurality of pockets, inserting a staple into each of said plurality of pockets through each of said pocket entrance openings.

3. The process of claim 1 including locking each said staple driver within said corresponding one of said plurality of pockets to prevent displacement of each said staple driver through a corresponding one of said pocket entrance openings.

4. The process of claim 3 wherein said locking step includes plastically deforming said pocket entrance openings to a different geometric shape or size which prevents displacement of each said staple driver from said plurality of said pockets by gravity.

5. The process of claim 4 wherein said cartridge is formed of material, said deforming step includes pushing a chisel blade into the material of said cartridge adjacent each of said plurality of pockets to alter the shape of each of said pocket entrance openings.

6. The process of claim 5 wherein said cartridge is formed of thermoplastic resin, heating said chisel to a temperature below the melting point of said resin before pushing said heated chisel into the material of said cartridge.

7. The process of claim 6 wherein said resin comprises phenylene oxide having a melting point above 375° F., and said heating step includes heating said chisel to a temperature in the range of about 325° F. to about 375° F.

8. The process of claim 7 including forming each said chisel to have two surfaces converging to form a chisel cutting edge, aligning each said chisel generally parallel with said channel, one surface of each of said chisel surfaces facing toward one of said plurality of pockets, configuring each said one surface as a concave surface diverging from said chisel cutting edge in a direction to extend said concave surface over said pocket entrance openings.

* * * * *